(12) United States Patent
Matsuda

(10) Patent No.: US 7,535,987 B2
(45) Date of Patent: May 19, 2009

(54) X-RAY CT APPARATUS

(75) Inventor: Keiji Matsuda, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/427,633

(22) Filed: Jun. 29, 2006

(65) Prior Publication Data

US 2007/0003005 A1    Jan. 4, 2007

(30) Foreign Application Priority Data

Jun. 30, 2005 (JP) ............................. 2005-191922

(51) Int. Cl.
*A61B 6/03* (2006.01)
*G21K 3/00* (2006.01)

(52) U.S. Cl. .............................. 378/7; 378/16; 378/159

(58) Field of Classification Search .................... 378/4, 378/9, 15, 901, 159, 7, 16
See application file for complete search history.

(56) References Cited

U.S. PATENT DOCUMENTS

| | | | |
|---|---|---|---|
| 3,717,768 A * | 2/1973 | Edholm et al. ............... 378/159 |
| 4,288,695 A * | 9/1981 | Walters et al. ................. 378/5 |
| 5,608,772 A * | 3/1997 | Nobuta et al. ................. 378/15 |
| 2003/0076920 A1* | 4/2003 | Shinno et al. .................. 378/4 |
| 2004/0034269 A1 | 2/2004 | Ozaki |
| 2005/0013411 A1* | 1/2005 | Yahata et al. ............... 378/156 |
| 2006/0023832 A1* | 2/2006 | Edic et al. ...................... 378/7 |

FOREIGN PATENT DOCUMENTS

| | | |
|---|---|---|
| CN | 1411787 A | 4/2003 |
| CN | 1575766 A | 2/2005 |
| JP | 6-315480 | 11/1994 |
| JP | 2974155 B2 * | 9/1999 |
| JP | 2004-73406 | 3/2004 |

OTHER PUBLICATIONS

U.S. Appl. No. 11/427,633, filed Jun. 29, 2006, Matsuda.
U.S. Appl. No. 11/456,682, filed Jul. 11, 2006, Matsuda.

* cited by examiner

*Primary Examiner*—Chih-Cheng G Kao
(74) *Attorney, Agent, or Firm*—Oblon, Spivak, McClelland, Maier & Neustadt, P.C.

(57) ABSTRACT

An X-ray CT apparatus includes a plurality of X-ray tubes, a plurality of X-ray detectors corresponding to the plurality of X-ray tubes, respectively, a support mechanism which supports the X-ray tubes and the X-ray detectors to allow the X-ray tubes and the X-ray detectors to rotate about a single rotation axis, a reconstruction unit which reconstructs image data on the basis of outputs from the X-ray detectors, and a plurality of filters which are respectively provided for the plurality of X-ray tubes and each have a characteristic in which an X-ray path length changes along a curve approximate to an inverted Gaussian curve from the rotation center to the two ends of an X-ray beam.

10 Claims, 8 Drawing Sheets

US 7,535,987 B2

X-RAY CT APPARATUS

CROSS-REFERENCE TO RELATED APPLICATIONS

This application is based upon and claims the benefit of priority from prior Japanese Patent Application No. 2005-191922, filed Jun. 30, 2005, the entire contents of which are incorporated herein by reference.

BACKGROUND OF THE INVENTION

1. Field of the Invention

The present invention relates to a multi-tube type X-ray CT apparatus comprising a plurality of pairs of X-ray tubes and X-ray detectors, and a filter.

2. Description of the Related Art

An X-ray CT apparatus (X-ray computed tomography apparatus) reconstructs a tomogram on the basis of a plurality of projection data sets acquired from a plurality of directions by rotation of a pair of an X-ray tube and a detector. A multi-tube type X-ray CT apparatus comprises a plurality of pairs. A multi-tube type X-ray CT apparatus is disclosed in, for example, Jpn. Pat. Appln. KOKAI Publication No. 2004-73406. The apparatus disclosed in Jpn. Pat. Appln. KOKAI Publication No. 2004-73406 includes an X-ray tube for medical treatment and an X-ray tube for data acquisition.

As shown in FIG. 4, in a multi-tube type X-ray CT apparatus, it is a problem that scattered radiation originating from X-rays generated by an X-ray tube 122 (121) of one pair is detected by an X-ray detector 131 (132) of the other pair.

The adverse effect of this detection is not small because scattered radiation generated by portions β1 and β2 of the surface of a subject P directly reach the X-ray detectors 131 and 132 without being attenuated by the subject P.

Note that filters (to be also referred to as wedge filters) are arranged between the X-ray tubes 121 and 122 and the subject P. As shown in FIG. 5A, each of the filters F1 and F2 has a sectional structure which has a thin middle portion and thick peripheral portions and whose thickness changes arcuately in accordance with changes in spread angle θ. More specifically, the filters F1 and F2 are designed such that the intensities of X-rays transmitted through the filters F1 and F2 and a cylindrical homogeneous phantom become almost constant, as shown in FIG. 5B.

BRIEF SUMMARY OF THE INVENTION

It is an object of the present invention to reduce the influence of scattered radiation originating from X-rays from a mating pair in a multi-tube type X-ray CT apparatus comprising a plurality of pairs of X-ray tubes and detectors.

According to a first aspect of the present invention, there is provided an X-ray CT apparatus comprising a plurality of X-ray tubes, a plurality of X-ray detectors corresponding to the plurality of X-ray tubes, respectively, a support mechanism which supports the X-ray tubes and the X-ray detectors to allow the X-ray tubes and the X-ray detectors to rotate about a single rotation axis, a reconstruction unit which reconstructs image data on the basis of outputs from the X-ray detectors, and a plurality of filters which are respectively provided for the plurality of X-ray tubes and each have a characteristic in which an X-ray path length changes along a curve approximate to an inverted Gaussian curve from the rotation center to two ends of an X-ray beam.

According to a second aspect of the present invention, there is provided an X-ray CT apparatus comprising a plurality of X-ray tubes, a plurality of X-ray detectors corresponding to the plurality of X-ray tubes, respectively, a support mechanism which supports the X-ray tubes and the X-ray detectors to allow the X-ray tubes and the X-ray detectors to rotate about a single rotation axis, a reconstruction unit which reconstructs image data on the basis of outputs from the X-ray detectors, and a plurality of filters which are respectively provided for the plurality of X-ray tubes and each have a characteristic in which an intensity of X-rays transmitted through each filter changes along a curve approximate to a Gaussian curve from the rotation center to two ends.

According to a third aspect of the present invention, there is provided an X-ray CT apparatus comprising a plurality of X-ray tubes, a plurality of X-ray detectors corresponding to the plurality of X-ray tubes, respectively, a support mechanism which supports the X-ray tubes and the X-ray detectors to allow the X-ray tubes and the X-ray detectors to rotate about a single rotation axis, a reconstruction unit which reconstructs image data on the basis of outputs from the X-ray detectors, and a plurality of filters which are respectively provided for the plurality of X-ray tubes and each have a characteristic in which an intensity of X-rays transmitted through the filter and a cylindrical homogeneous phantom decreases curvilinearly from the rotation center to two ends.

According to a fourth aspect of the present invention, there is provided an X-ray CT apparatus comprising a plurality of X-ray tubes, a plurality of X-ray detectors corresponding to the plurality of X-ray tubes, respectively, a support mechanism which supports the X-ray tubes and the X-ray detectors to allow the X-ray tubes and the X-ray detectors to rotate about a single rotation axis, a reconstruction unit which reconstructs image data on the basis of outputs from the X-ray detectors, and a plurality of filters which are respectively provided for the plurality of X-ray tubes and each have a characteristic in which an intensity of X-rays transmitted through the filter exceeds 90% of a maximum intensity at the rotation center at a middle portion less than 10 cm away from the rotation center, and an intensity at a peripheral portion more than 20 cm away from the rotation center is less than 50% of the maximum intensity at the rotation center.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described in detail below with reference to the views of the accompanying drawing.

Figure 1:
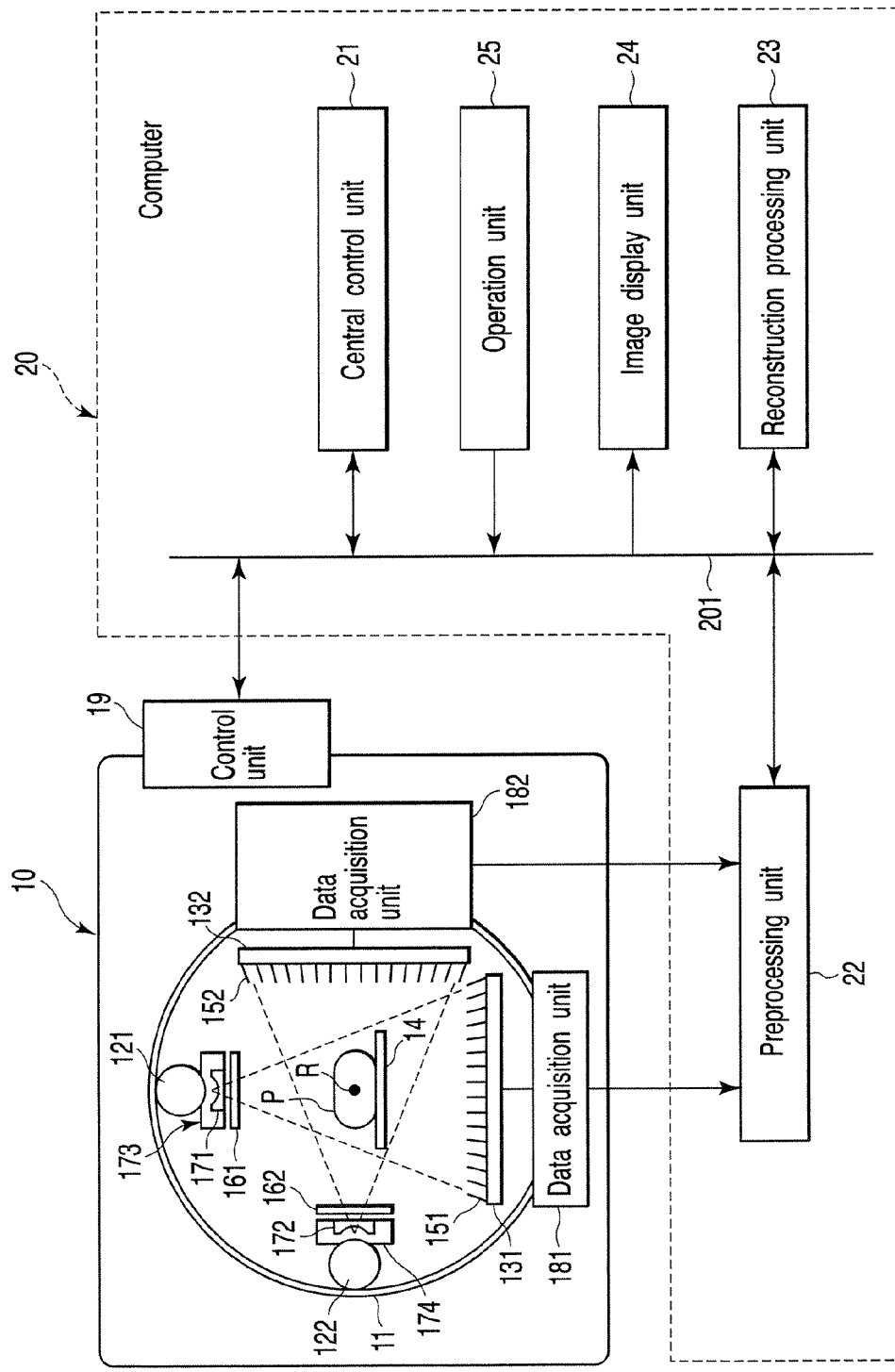
FIG. 1 is a block diagram showing the overall arrangement of an X-ray CT apparatus according to an embodiment of the present invention.

FIG. 1 is a block diagram showing the overall arrangement of an X-ray CT apparatus according to an embodiment of the present invention. Referring to FIG. 1, the X-ray CT apparatus (computed tomography apparatus) of this embodiment includes a gantry 10, a computer 20, and a bed (not shown). The gantry 10 is of a multi-tube type, on which a plurality of scanners including pairs of X-ray tubes and X-ray detectors are mounted. In this embodiment, this gantry will be described as a two-tube type gantry.

The gantry 10 is provided with a rotating frame 11. The rotating frame 11 rotates about a rotation axis R by a rotating mechanism. In the rotating frame 11, scanners comprising the first pair of an X-ray tube 121 and an X-ray detector 131 which are located to face each other and the second pair of an X-ray tube 122 and an X-ray detector 132 which are located to face each other are arranged every predetermined angle (e.g., 90°). An opening portion is formed in the central portion of the rotating frame 11. A subject P placed on a top 14 of the bed is inserted into the opening portion.

The X-ray detectors 131 and 132 are respectively provided with collimators 151 and 152 which face the X-ray tubes 121 and 122 to limit incident X-rays. Slits 161 and 162 are arranged between the X-ray tubes 121 and 122 and the rotation axis R. In addition, the X-ray tubes 121 and 122 are respectively provided with filters for scattered radiation reduction (to be also referred to as wedge filters) 171 and 172. The filters 171 and 172 are detachably supported on filter support mechanisms 173 and 174. These filters can be replaced with other filters having shapes conforming to the shapes of subjects.

Outputs from the X-ray detectors 131 and 132 are sent to data acquisition units 181 and 182 and supplied to a preprocessing unit (to be described later) of the computer 20. The gantry 10 is also provided with a control unit 19, which performs control on the tube voltages of the X-ray tubes 121 and 122, rotation control on the rotating frame 11, and the like.

The computer 20 includes a central control unit 21, to which a preprocessing unit 22, reconstruction processing unit 23, image display unit 24, operation unit 25, and the like are connected through data/control bus lines 201. X-rays transmitted through the subject P are converted into electrical signals by the X-ray detectors 131 and 132, and are amplified and converted into digital data by the data acquisition units 181 and 182. The projection data are then supplied to the preprocessing unit 22. The preprocessing unit 22 performs processing such as correction of signal intensities and correction of signal omissions, and outputs the imaging data onto the bus lines 201.

The central control unit 21 controls the operation of each unit of the computer 20 and controls the control unit 19 of the gantry 10. The reconstruction processing unit 23 reconstructs tomogram data on the basis of projection data. The image display unit 24 includes a display which displays medical images and the like. The operation unit 25 is used by a doctor to input information such as the state of a patient, an examination method, and the like.

Figure 2:
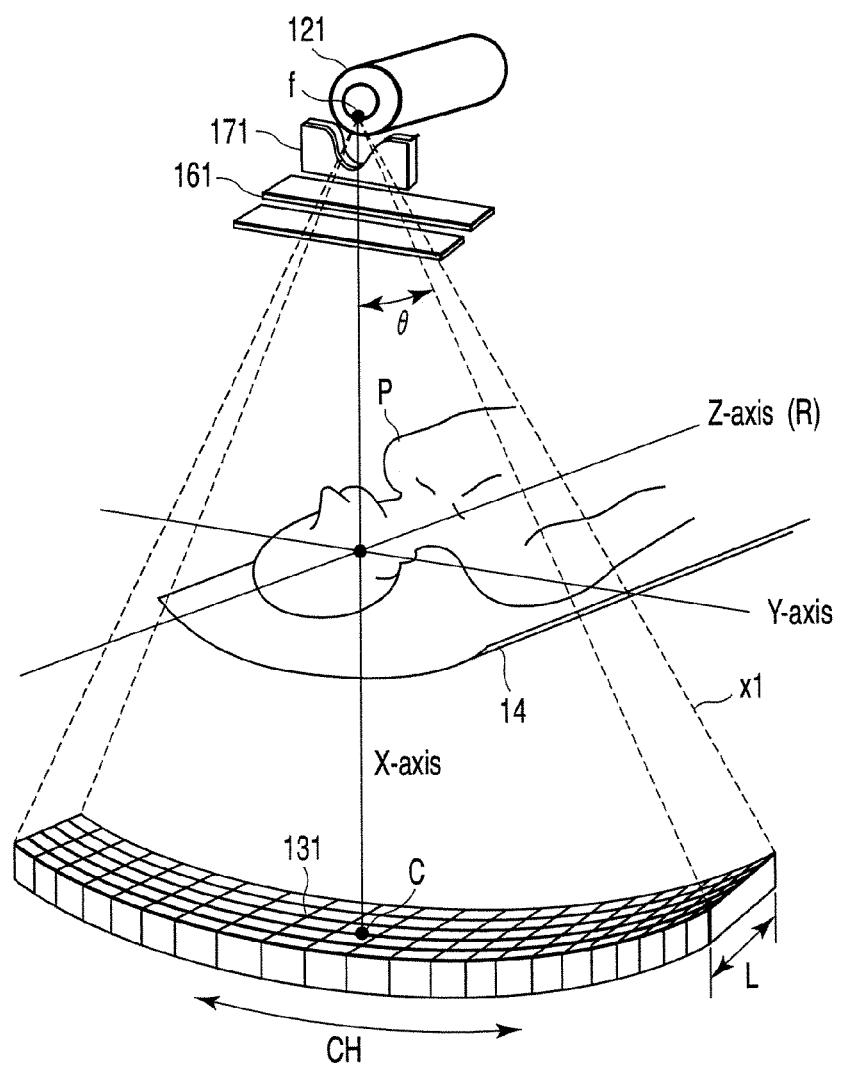
FIG. 2 is a perspective view showing the arrangement of the main part of the X-ray CT apparatus in FIG. 1.

FIG. 2 is an enlarged view of the arrangement of the main part of this embodiment. This view shows the arrangement of a scanner including the first pair of the X-ray tube 121 and the X-ray detector 131, and the arrangement of a scanner including the second pair of the X-ray tube 122 and the X-ray detector 132. FIG. 2 representatively shows the first pair of the X-ray tube 121 and the X-ray detector 131. The second pair of the X-ray tube 122 and the X-ray detector 132 has the same arrangement as that of the first pair except that the second pair is placed with its imaging reference line (X-axis) being shifted from that of the first pair by an angle of 90°, and hence an illustration of the second pair will be omitted in FIG. 2.

Referring to FIG. 2, the slit 161 is placed to face the X-ray tube 121. The thickness of an X-ray beam is determined by the opening degree of the slit 161. The maximum value of the spread angle θ of X-rays is determined in advance in accordance with the number of channels x channel pitch of the X-ray detector 131. The spread angle θ of X-rays is defined as the angle defined by the X-axis (imaging reference line) and an X-ray beam from an X-ray focal point f. The X-axis passes through the X-ray focal point f of the X-ray tube 121 and a central point C of the detection surface of the X-ray detector 131. The Z-axis coincides with the rotation axis R. In imaging operation, the subject P is placed such that the body axis almost coincides with the Z-axis. The Y-axis is an axis perpendicular to the X-axis and the Z-axis. The X-, Y-, and Z-axes constitute a rotating coordinate system centered on the Z-axis.

The X-ray detector 131 includes many detection elements arrayed in the channel direction (CH) and the column direction (Z-axis direction). The channel direction (CH) is defined as the direction of an arc centered on the X-ray focal point f. The X-ray detector 131 detects an X-ray beam x1 transmitted through the subject P.

The collimator 151 (see FIG. 1) is mounted on the X-ray detector 131. The collimator 151 has a plurality of thin collimate plates made of metal such as molybdenum which are arranged in a direction to converge to the focal point f of the X-ray tube 121 as a component of the pair. The collimator 151 limits the direction of X-rays striking the X-ray detector 131 to a direction from the focal point f of the X-ray tube 121 as a component of the pair. The multi-tube type X-ray CT apparatus is smaller in rotation angle necessary to obtain the reconstructed image than that of a single tube type apparatus, and can shorten the time required to acquire projection data, and hence can improve the time resolution. This apparatus is therefore suitable for the diagnosis of the heart portion of the subject P and a movement portion around the heart portion.

The filter 171 for scattered radiation reduction is placed between the X-ray tube 121 and the slit 161. The filter 171 is detachably supported on the filter support mechanism 173. The filter 171 has a function of reducing low-energy components which are absorbed by the subject P and do not reach the X-ray detector 131 and a function of aligning the dynamic range of the X-ray detector 131 and the like in a surrounding area of the subject P with that in a central area of the subject P as much as possible by allowing the difference in X-ray absorption between the surrounding area of the subject P and the central area of the subject P.

As a function unique to this embodiment, the filter 171 also has a function of effectively reducing the influence of scattered radiation originating from X-rays generated by the X-ray tube 122 of the other pair. Scattered radiation which is generated when X-rays generated by the X-ray tube 122 of the other pair are scattered by the body surface of the subject and directly strike the X-ray detector 131 without being attenuated produces the most adverse effect. Scattered radiation which is scattered by an open portion (a portion β2 of the body surface in FIG. 4) viewed from both the X-ray tube 122 and the X-ray detector 131 is directly detected by the X-ray detector 131 without being transmitted through the subject P and attenuated.

Although described in detail later, as typically shown in FIG. 3, a recess portion 17a is formed in a portion of the filter 171 which faces the X-ray tube 121. The recess portion has a curved surface shape with a thin middle portion and thick peripheral portions, and the curved surface has a geometrical shape with a steep slope extending from a bottom portion to a top portion.

X-rays from the X-ray tube are transmitted through the middle portion of the filter 171 at a high transmittance, and are transmitted through the peripheral portions at a low transmittance. That is, the amount of X-rays which are transmitted through the filter 171 and strike the central portion of the X-ray detector 131 of the self-pair in the channel direction is large, and the amount of X-rays which strike the peripheral portions in the channel direction is small.

Figure 4:
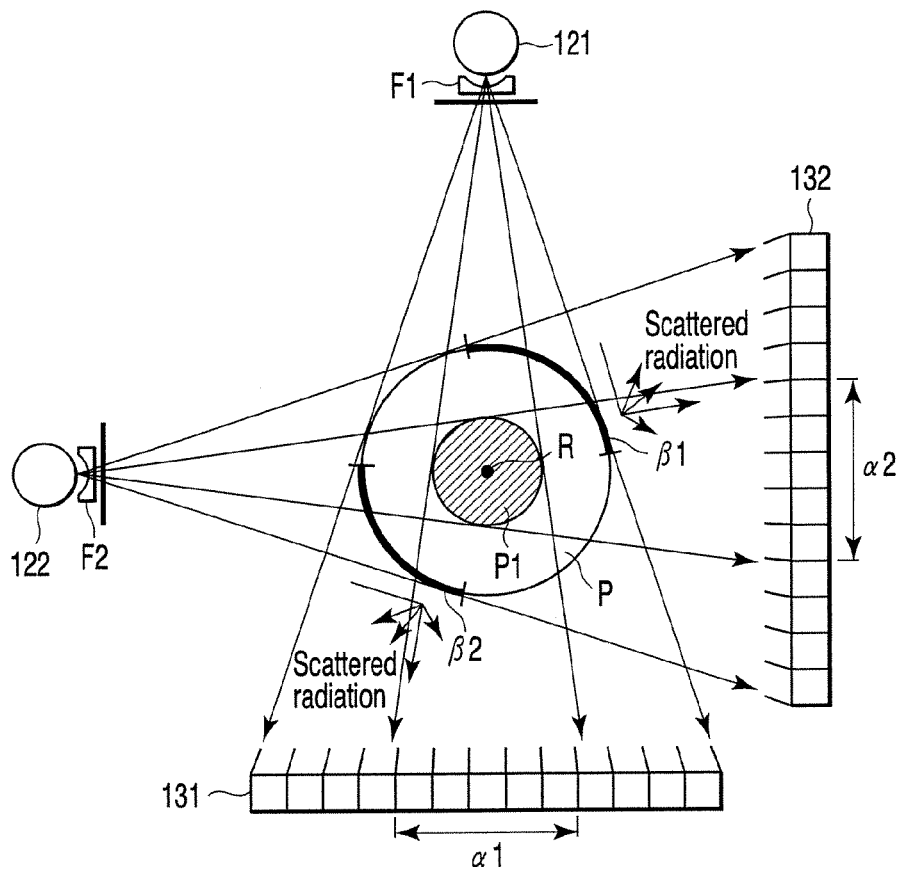
FIG. 4 is a view for explaining the influence of scattered radiation in the prior art.

Such effects of the filters 171 and 172 will be described next with reference to FIGS. 4, 5, 6, and 7. FIG. 4 is a view for explaining the influence of scattered radiation from the X-ray tube of the other pair, showing a case wherein the conventional filters F1 and F2 are used. FIGS. 6 and 7 are views for explaining the effect of reducing scattered radiation by using the filters 171 and 172 in this embodiment.

In the case shown in FIG. 4, when a diagnosis target of the subject P is represented by p1 (e.g., the heart portion which is the portion displayed in dark color in FIG. 4) and the body surface is represented by p2, X-rays from the X-ray tube 121 which are applied to the subject through a filter F1 and the slit 161 and are detected by the X-ray detector 131, and X-rays from the X-ray tube 122 which are applied to the subject through a filter F2 and the slit 162 and are detected by the X-ray detector 132. At this time, the ranges of X-rays transmitted through the main organ (target p1) are defined as main scanning ranges α1 and α2.

Figure 5A:
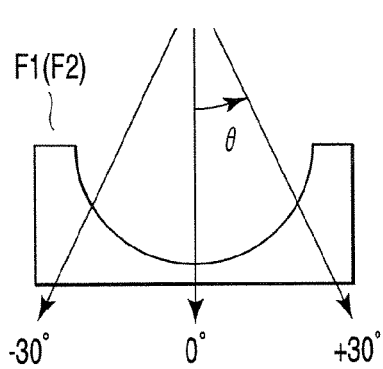
FIG. 5A is a view showing a sectional shape of a conventional filter.
Figure 5B:
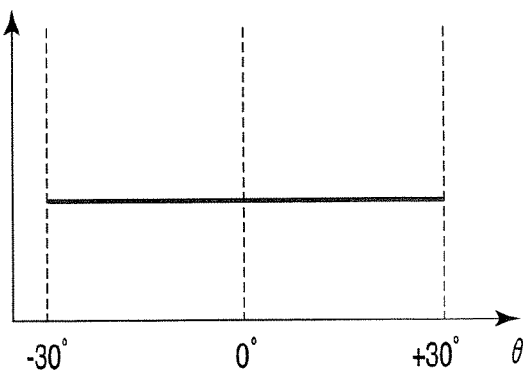
FIG. 5B is a graph showing changes in the intensity of X-rays transmitted through the filter in FIG. 5A and a homogeneous phantom as a function of a spread angle θ.
Figure 6:
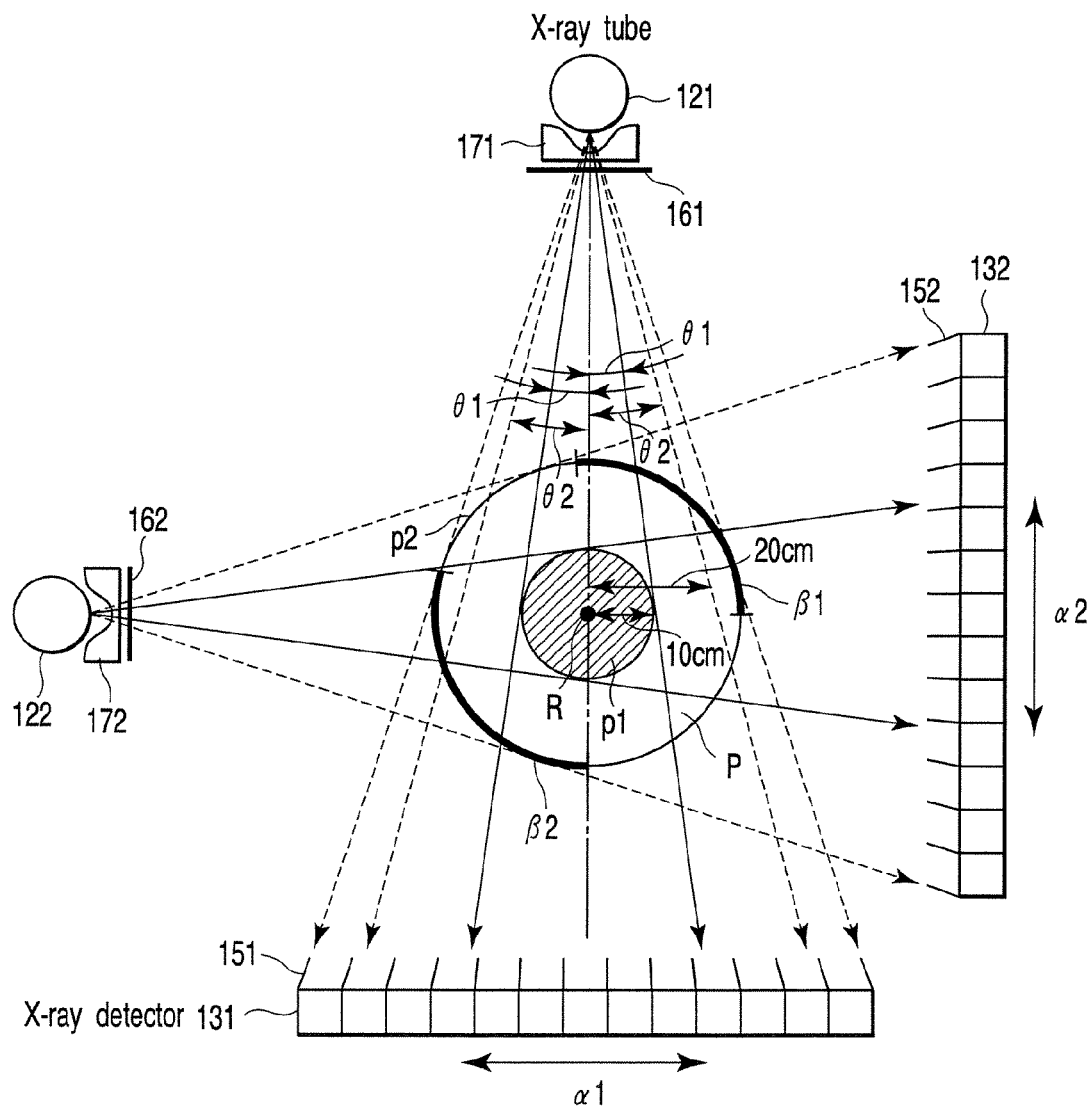
FIG. 6 is a view for supplementary explanation of the function of the filter in FIG. 1.

The thickness of each of the conventional filters F1 and F2 is changed and its inner surface is designed into an almost arcuated shape as shown in FIG. 5A such that the intensity of X-rays transmitted through each of the filters F1 and F2 and the cylindrical homogeneous phantom becomes constant with respect to the X-ray spread angle θ.

Scattered radiation originating from X-rays from the X-ray tube 122 of the other pair strikes the X-ray detector 131. Likewise, scattered radiation originating from X-rays from the X-ray tube 121 of the other pair strikes the X-ray detector 132. At this time, scattered radiation which particularly influences the other pair is X-rays scattered by the open surface portions β1 and β2. Scattered radiation scattered by portions other than the surface portions β1 and β2 is attenuated within the subject, and hence has a small influence.

Figure 3:
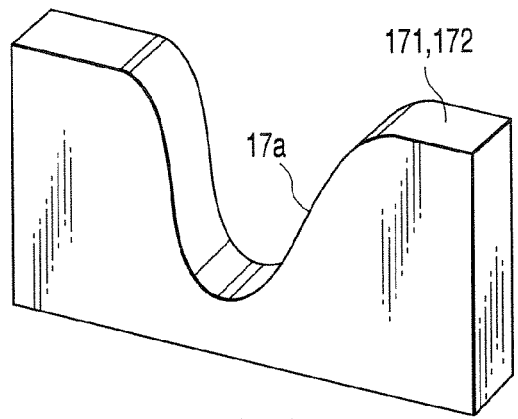
FIG. 3 is a perspective view of a filter in FIG. 1.

When the filters 171 and 172 shown in FIG. 3 are set for the X-ray tubes 121 and 122 as shown in FIG. 6, since the peripheral portions of the filters 171 and 172 are much thicker than the central portions, X-rays are transmitted through the peripheral portions at a transmittance considerably lower than that of the central portions. For example, the transmittance of the peripheral portions decreases to about several % to 50% of that of the central portions.

Figure 7A:
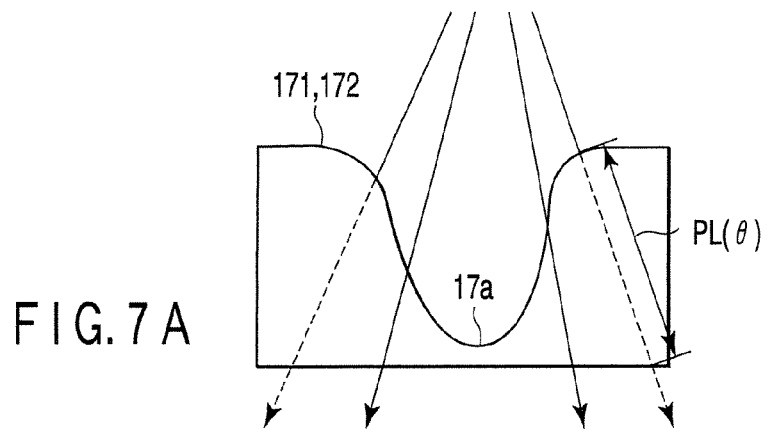
FIGS. 7A and 7B are views for explaining an X-ray path length.

That is, each of the filters 171 and 172 in this embodiment has a thin central portion, and the thickness steeply increases toward the peripheral portions as shown in FIG. 7A. In this structure, X-rays from the X-ray tube are transmitted through the middle portion of the filter 171 at a high transmittance, and the transmittance becomes lower than that of each of the conventional filters F1 and F2. That is, the amount of X-rays which are transmitted through the filter 171 and strike the central portion of the X-ray detector 131 of the self-pair in the channel direction is large, whereas the amount of X-rays which strike each peripheral portion of the X-ray detector 131 in the channel direction is smaller than that of the conventional filters F1 and F2.

Figure 7B:
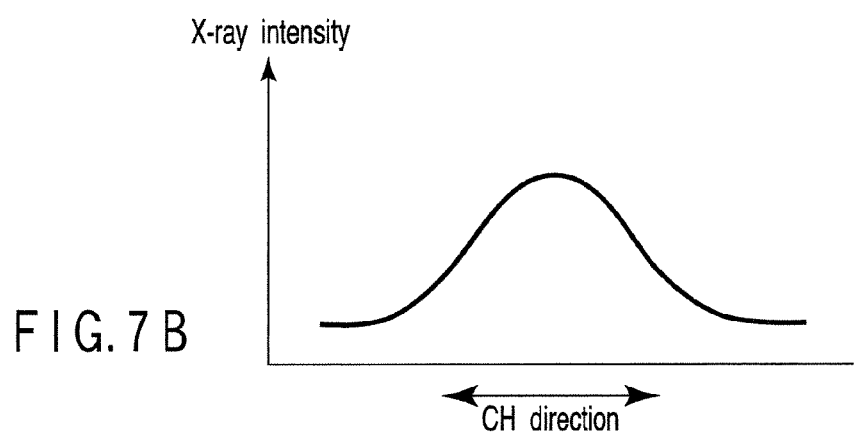

For this reason, as shown in FIG. 7B, when the subject P is inserted, the intensity of X-rays detected by the X-ray detectors 131 and 132 of the respective pairs is high at the middle portions in the channel direction (CH), and decreases toward the peripheral portions. Therefore, the dose of radiation applied to near the main organ portion p1 of the subject P can be imaged without being hardly reduced. In addition, the amount of X-rays applied to the surface β2 of the subject P is greatly reduced, and hence scattered radiation at the portions β1 and β2 is greatly reduced. Even if the transmittance of the peripheral portions with respect to X-rays is reduced, no significant problem arises in diagnosis of the main organ.

With this operation, when the subject P is inserted, scattered radiation which adversely influences the detection results in the main scanning ranges α1 and α2 which are detected by the X-ray detectors 131 and 132 can be considerably reduced. In addition, the main organ can be properly diagnosed without changing the dose of X-rays near the main organ portion p1. Furthermore, this can reduce the exposure dose on the skin of the human body which is susceptible to adverse effects from X-rays.

Figures 8A, 8B:
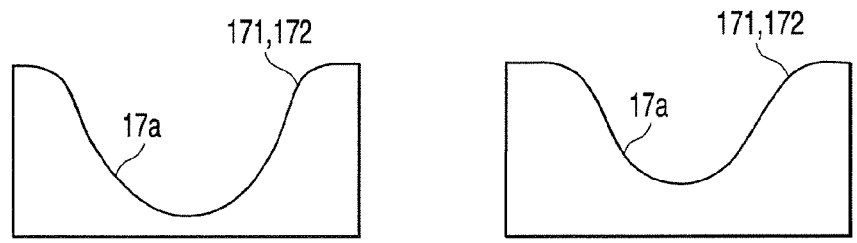
FIG. 8A is a view showing a sectional shape of the filter in FIG. 1.
FIG. 8B is a view showing another sectional shape of the filter in FIG. 1.
Figure 8C:
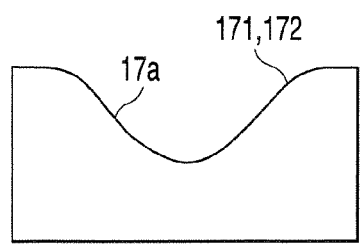
FIG. 8C is a view showing still another sectional shape of the filter in FIG. 1.

FIGS. 8A, 8B, and 8C show the structures of filters 171 and 172 in another embodiment of the present invention. When X-rays are applied to the subject P, since different organs have different transmittances, a plurality of filters 171 and 172 having curved surfaces 17a with different curvatures are prepared to allow selection of any one of the filters in accordance with the diagnosis of each organ. This makes it possible to perform more accurate diagnosis.

For example, a plurality of types of filters are prepared in the X-ray CT apparatus, and one of the filters is selected by electric operation when imaging is to be performed. In this case, in order to reduce the influence of scattered radiation, each of the filters 171 and 172 is shaped such that the middle portion is thin, and the peripheral portions are thick, and has a characteristic in which the intensity of X-rays detected by each of X-ray detectors 131 and 132 is high at the middle portion in the channel direction (CH), and is low at the peripheral portions.

Figure 9:
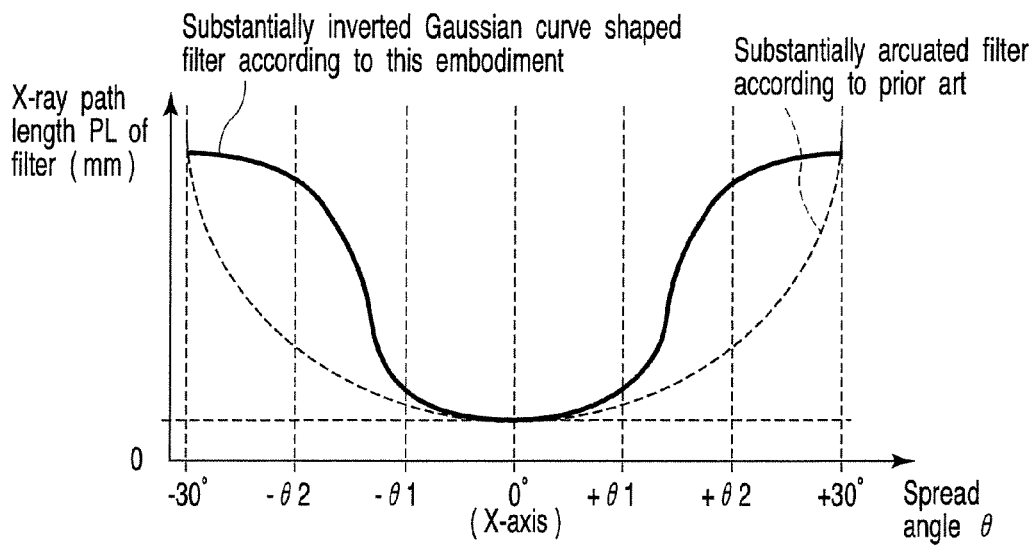
FIG. 9 is a graph showing changes in an X-ray path length PL of the filter in FIG. 1 as a function of the spread angle θ.

The structure of the filter 171 will be described in more detail. The structure of the filter 172 is equivalent to that of the filter 171, and hence a description thereof will be omitted. FIG. 9 shows changes in an X-ray path length PL of the filter 171 as a function of a spread angle θ. The X-ray path length PL corresponds to a thickness, and to be more precise, is defined as a distance that an X-ray beam passes through the filter 171 as shown in FIG. 7A. θ1 represents the spread angle of an X-ray beam tangent to a circle which is centered on a rotation axis R and has a radius of 10 cm. θ2 represents the spread angle of an X-ray beam tangent to a circle which is centered on the rotation axis R and has a radius of 20 cm. The filter 171 has a structure with a characteristic in which the X-ray path length PL gradually changes from the rotation axis R to the two ends of an X-ray beam, i.e., with an increase in the absolute value of the spread angle θ, along a curve approximate to the inverted shape of a Gaussian curve. As compared with a conventional filter having shape approximated to circular arc, the X-ray path length PL of the filter 171 changes almost in the same manner up to a spread angle ±θ1, but steeply increases in the range exceeding the spread angle ±θ1.

Figure 10:
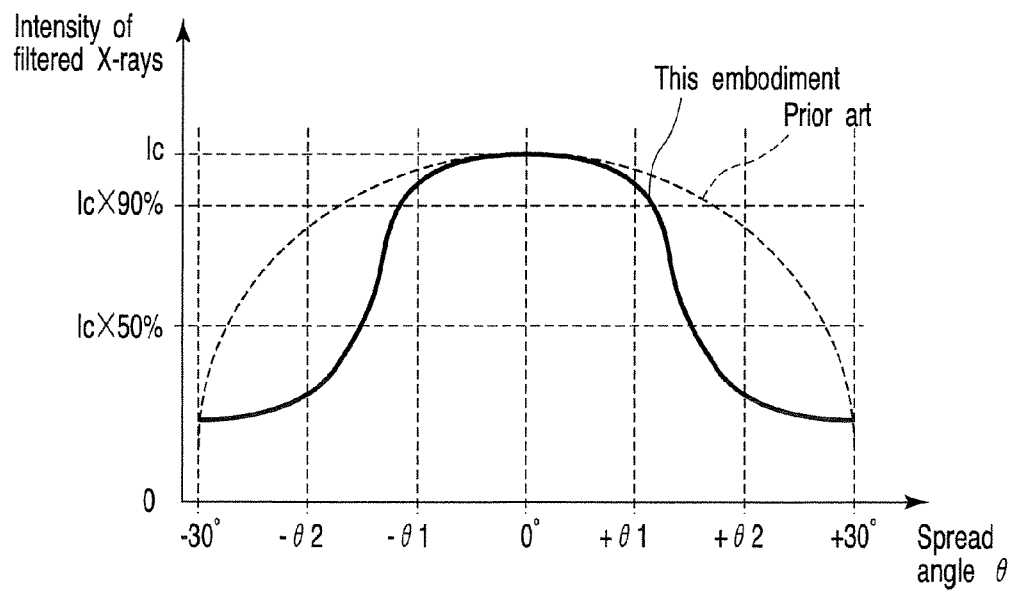
FIG. 10 is a graph showing changes in the intensity of X-rays transmitted through the filter in FIG. 1 as a function of the spread angle θ.

FIG. 10 shows changes in the intensity of X-rays transmitted through the filter 171 as a function of the spread angle θ. The filter 171 has a structure with a characteristic in which the intensity of X-rays transmitted through the filter 171 gradually changes from the rotation axis R to the two ends of an X-ray beam, i.e., with an increase in the absolute value of the spread angle θ, along a curve approximate to a Gaussian curve. As compared with a conventional filter having shape approximated to circular arc, the intensity of X-rays transmitted through the filter 171 changes almost in the same manner up to a spread angle ±θ1, but steeply decreases in the range exceeding the spread angle ±θ1. More specifically, the filter 171 has a characteristic in which the intensity of X-rays transmitted through the filter 171 exceeds 90% of a maximum intensity Ic at a middle portion less than 10 cm away from the rotation axis R, and becomes less than 50% of the maximum intensity Ic at peripheral portions more than 20 cm away from the rotation axis R. Note that the intensity of X-rays transmitted through a conventional typical filter exceeds 50% of the maximum intensity Ic at a position 20 cm away from the rotation axis R, and becomes lower than 50% of the maximum intensity Ic at almost end portions.

Figure 11:
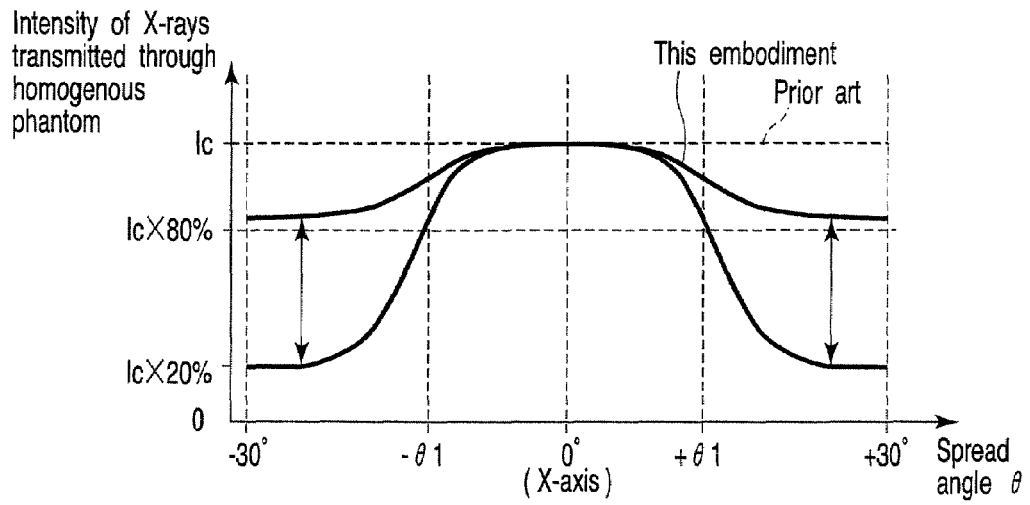
FIG. 11 is a graph showing changes in the intensity of X-rays transmitted through the filter in FIG. 1 and a homogenous phantom as a function of the spread angle θ.

FIG. 11 shows changes in the intensity of X-rays transmitted through the filter 171 and the cylindrical homogeneous phantom as a function of the spread angle θ. The filter 171 has a structure with a characteristic in which the intensity of X-rays transmitted through the filter 171 and the homogeneous phantom gradually decreases curvilinearly from the rotation axis R to the two ends of an X-ray beam, i.e., with an increase in the absolute value of the spread angle θ. As compared with a conventional arcuated filter, although X-rays transmitted through the conventional filter and the homogenous phantom exhibit an almost constant value, the intensity of X-rays transmitted through the filter 171 of this embodiment and the homogeneous phantom is not constant, but gradually decreases in a range exceeding the spread angle ±θ1. More specifically, the filter 171 has a characteristic in which the intensity of X-rays transmitted through the filter 171 and the homogeneous phantom gradually changes within the range of the maximum intensity Ic and 20-80% thereof.

Figure 12:
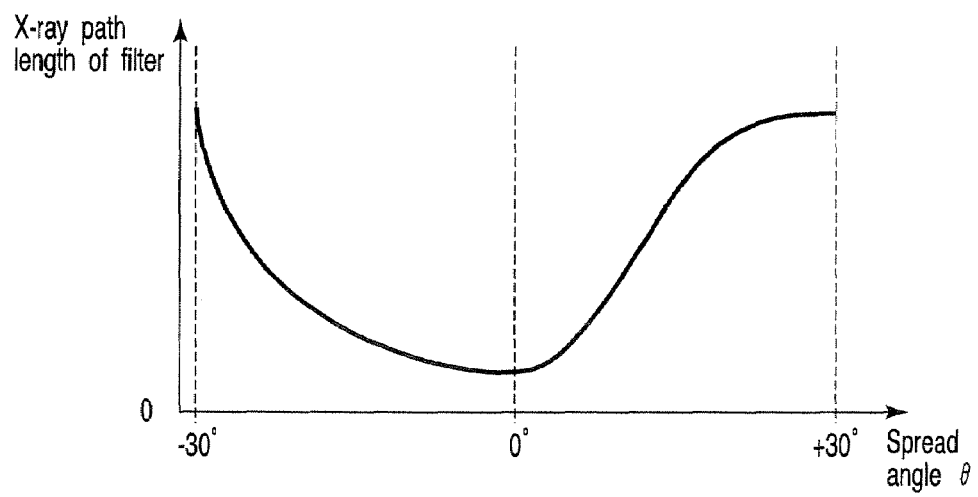
FIG. 12 is a view showing changes in the X-ray path length PL of a modification of the filter in FIG. 1 as a function of the spread angle θ.

As described above, scattered radiation which is scattered by an open portion (the portion β2 of the body surface in FIG. 4) viewed from both the X-ray tube 122 and the X-ray detector 131 strongly influences an output from the X-ray detector 131. As exemplified by FIG. 12, a portion of the filter 171 which corresponds to the open portion β2, i.e., an almost half of the X-ray detector 132 in the spread angle range of 0° to +30°, is provided with a new characteristic in which a path length changes along an inverted Gaussian curve, and an almost half of the X-ray detector 132 which corresponds to the opposite side to the open portion β2 and is located in the spread angle range of −30° to 0°, which is less influenced by scattered radiation, is provided with the same characteristic as that in the prior art in which a path length changes arcuately. In this case, the influence of scattered radiation from the X-ray tube of the other pair can be suppressed, and a reduction in S/N ratio can be suppressed. Note that the characteristic of the filter 172 is inverted horizontally.

Figure 13:
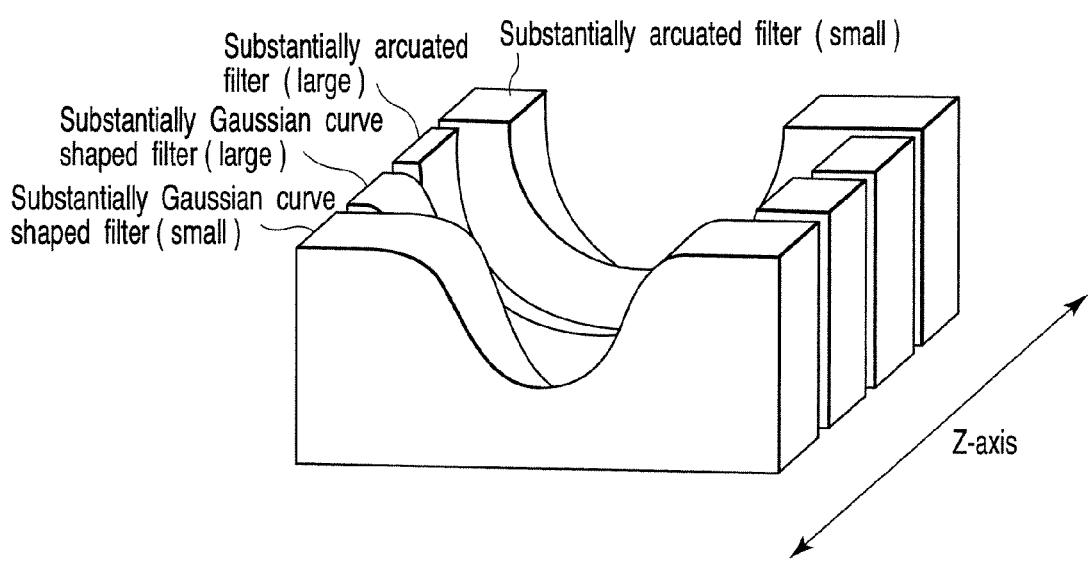
FIG. 13 is a perspective view showing another example of the arrangement of a filter support mechanism in FIG. 1.

FIG. 13 shows a modification of the filter support mechanism 173. A filter support mechanism 174 has the same structure as that of the filter support mechanism 173, and hence a description thereof will be omitted. The filter support mechanism 173 has a structure that allows a plurality of filters with different characteristics to be mounted, and a mechanism of sliding a plurality of filters in the Z-axis direction. With this sliding operation, one of the filters is arranged between the X-ray tube and the detector. This makes it possible to selectively use several filters. The following four filters are preferably mounted on the filter support mechanism 173.

The first filter has a characteristic unique to this embodiment, in which the intensity of X-rays transmitted through the filter gradually changes along a curve approximate to a Gaussian curve with an increase in the absolute value of the spread angle θ. The range in which the intensity of X-rays transmitted through this filter exceeds 90% of the maximum value Ic is relatively narrow. For example, this range has a radium of 8 cm.

The second filter has a characteristic unique to this embodiment, in which the intensity of X-rays transmitted through the filter gradually changes along a curve approximate to a Gaussian curve with an increase in the absolute value of the spread angle θ. The range in which the intensity of X-rays transmitted through this filter exceeds 90% of the maximum value Ic is relatively wide. For example, this range has a radium of 10 cm.

The third filter has a characteristic unique to the prior art, in which the intensity of X-rays transmitted through the filter gradually changes along an almost arcuated shape with an increase in the absolute value of the spread angle θ. The range in which the intensity of X-rays transmitted through this filter exceeds 90% of the maximum value Ic is relatively wide. For example, this range has a radium of 16 cm.

The fourth filter has a characteristic unique to the prior art, in which the intensity of X-rays transmitted through the filter gradually changes along an almost arcuated shape with an increase in the absolute value of the spread angle θ. The range in which the intensity of X-rays transmitted through this filter exceeds 90% of the maximum value Ic is relatively narrow. For example, this range has a radium of 10 cm.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus, comprising:
a plurality of X-ray tubes;
a plurality of X-ray detectors corresponding to said plurality of X-ray tubes, respectively, each X-ray tube and corresponding X-ray detector forming a pair;
a support mechanism which supports the X-ray tubes and the X-ray detectors to allow the X-ray tubes and the X-ray detectors to rotate about a single rotation axis;
a reconstruction unit which reconstructs image data on the basis of outputs from the X-ray detectors; and
a plurality of filters corresponding to said plurality of X-ray tubes, each filter having a characteristic in which an X-ray path length changes as a function substantially equal to an inverted Gaussian curve from the rotation center to two ends of an X-ray beam so as to reduce scattering radiation originating from X-rays generated by an X-ray tube of a first pair, but detected by an X-ray detector of a second, different pair;
wherein said each filter has a characteristic in which an intensity of X-rays transmitted through the filter exceeds 90% of a maximum intensity at the rotation center at a middle portion less than 10 cm away from the rotation center, and an intensity at a peripheral portion more than 20 cm away from the rotation center is less than 50% of the maximum intensity at the rotation center.

2. An apparatus according to claim 1, further comprising a mechanism which attaches/detaches the filters.

3. An apparatus according to claim 1, which further comprises a plurality of slits which are respectively provided for said plurality of X-ray tubes and limit X-ray thicknesses, and in which
the filter is placed between the X-ray tube and the slit.

4. An apparatus according to claim 1, wherein said each filter further has a characteristic in which an intensity of X-rays transmitted through said each filter changes as a function substantially equal to a Gaussian curve from the rotation center to two ends of an X-ray beam.

5. An apparatus according to claim 1, wherein said each filter further has a characteristic in which an intensity of X-rays transmitted through said each filter and a cylindrical homogeneous phantom changes curvilinearly from the rotation center to two ends of an X-ray beam.

6. An apparatus according to claim 1, wherein said each filter has a curved surface shape with a thickness of a central portion being small, and a thickness gradually increasing toward peripheral portions.

7. An X-ray CT apparatus, comprising:
a plurality of X-ray tubes;
a plurality of X-ray detectors corresponding to said plurality of X-ray tubes, respectively, each X-ray tube and corresponding X-ray detector forming a pair;
a support mechanism which supports the X-ray tubes and the X-ray detectors to allow the X-ray tubes and the X-ray detectors to rotate about a single rotation axis;
a reconstruction unit which reconstructs image data on the basis of outputs from the X-ray detectors; and
a plurality of filters corresponding to said plurality of X-ray tubes and each have a characteristic in which an intensity of X-rays transmitted through the filter exceeds 90% of a maximum intensity at the rotation center at a middle portion less than 10 cm away from the rotation center, and an intensity at a peripheral portion more than 20 cm away from the rotation center is less than 50% of the maximum intensity at the rotation center so as to reduce scattering radiation originating from X-rays generated by an X-ray tube of a first pair, but detected by an X-ray detector of a second, different pair.

8. A filter provided for an X-ray tube of an X-ray CT apparatus, which has a characteristic in which an X-ray path length changes as a function equal to an inverted Gaussian curve from a center to two ends.

9. The filter of claim 8, wherein the filter has a characteristic in which an intensity of X-rays transmitted through the filter and a cylindrical homogenous phantom gradually change such that the intensity at the ends of the X-ray beam is 20%-80% of the intensity at a rotation center.

10. A filter provided for an X-ray tube of an X-ray CT apparatus, which has a characteristic in which an intensity of X-rays transmitted through the filter exceeds 90% of a maximum intensity at a center throughout a middle portion less than 10 cm away from the center, and an intensity throughout a peripheral portion more than 20 cm away from the center is less than 50% of the maximum intensity at the center.

* * * * *